United States Patent [19]

Ray et al.

[11] 4,351,963

[45] Sep. 28, 1982

[54] ALIPHATIC OLEFIN OXIDATION USING CATALYST CONTAINING SN, P, O, LI

[75] Inventors: Gardner C. Ray; Paul W. Solomon, both of Bartlesville, Okla.

[73] Assignee: Phillips Petroleum Company, Bartlesville, Okla.

[21] Appl. No.: 228,038

[22] Filed: Jan. 23, 1981

[51] Int. Cl.³ .................. C07C 45/34; C07C 47/20
[52] U.S. Cl. ............................ 568/477; 568/476
[58] Field of Search .............. 568/477, 480, 476

[56] References Cited

U.S. PATENT DOCUMENTS

| | | | |
|---|---|---|---|
| 3,244,642 | 4/1966 | Gasson et al. | 568/477 |
| 3,359,325 | 12/1967 | Sennewald et al. | 568/450 |
| 3,524,824 | 8/1970 | Eden | 568/477 |
| 3,640,901 | 2/1972 | Walker | 568/477 |
| 3,703,550 | 11/1972 | Nolon et al. | 260/533 N |
| 3,789,078 | 1/1974 | Nolon et al. | 568/454 |
| 3,824,195 | 7/1974 | Pitzer | 568/477 |

FOREIGN PATENT DOCUMENTS 642920  6/1962  Canada ................. 568/477

*Primary Examiner*—Werren B. Lone

[57] ABSTRACT

A method for preparing aldehyde from aliphatic olefin in the presence of oxygen and a catalyst containing Sn, P, Li, and O.

6 Claims, No Drawings

ALIPHATIC OLEFIN OXIDATION USING CATALYST CONTAINING SN, P, O, LI

BACKGROUND OF THE INVENTION

This invention relates to oxidation of aliphatic olefins. In one aspect it relates to catalyzed oxidation reactions. In another aspect it relates to compositions containing lithium used as aliphatic olefin oxidation catalysts.

Acrolein and methacrolein are valuable starting materials for the synthesis of chemicals useful in textile finishings, paper treating and the manufacture of rubber chemicals, pharmaceuticals, plasticizers and synthetic resins. One of the largest single uses for acrolein has been the preparation of the amino acid, methionine. Acrolein and methacrolein can be prepared commercially by the oxidation of propylene and isobutylene using various type catalysts such as cuprous oxide, mixed oxides of bismuth, molybdenum and cobalt, oxides of antimony plus other metals, combinations including tungsten oxide and a silver selenide. Among other multiple-component catalyst systems that have been reported for the oxidation of propylene to acrolein are those reported in U.S. Pat. No. 3,359,325 which describes a catalyst system of $V_2O_5/SnO_2/P_2O_5$ for use in the air oxidation of propylene to acrolein in the presence of steam and U.S. Pat. No. 3,703,550 which discloses a process of air oxidation of propylene to acrolein using a catalyst that is based on the oxides of Sn and P to which is also added the oxides of Mo, Te and Fe. In none of the patents discussed above is lithium used in conjunction with other metals in an aliphatic olefin oxidation catalyst.

The catalyst system described in this invention has been known for use in the oxodehydrogenation of olefins. These catalysts have also been used in processes in which alkenylaromatics such as styrene are oxidized to aromatic aldehydes such as benzaldehyde, see U.S. Pat. No. 3,843,732, and the preparation of furfural, see U.S. Pat. No. 3,789,078.

It is an object of this invention to prepare aldehyde from aliphatic olefin. It is another object of this invention to provide a catalyst suitable for preparing aldehyde from aliphatic olefin.

Other aspects, objects and the various advantages of this invention will become apparent upon study of this specification and the appended claims.

STATEMENT OF INVENTION

According to this invention, a method for preparing aldehyde from aliphatic olefin is provided in which the aliphatic olefin is contacted with oxygen at an elevated temperature in the presence of a catalyst containing lithium as well as phosphorus, tin, and oxygen.

Aliphatic olefins useful in this invention are those materials represented by the formula

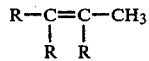

wherein each R can be hydrogen or any alkyl group having one to 8 carbon atoms, and each R can be the same or different from the other R's. Exemplary of such materials are: propylene, 2-methylpropene(isobutylene), 2-butene, 2-methyl-2-butene, 2,3-dimethyl-2-butene, 2-methyl-1-butene, 2-methyl-1-octene, 2-methyl-1-decene, and the like and mixtures thereof. Propylene and isobutylene are the preferred aliphatic olefins, because other aliphatic olefins may tend to produce some ketones in addition to unsaturated aldehydes.

The catalyst useful in this invention contains tin, phosphorous, oxygen and lithium. Preparation of this type of catalyst is described in U.S. Pat. Nos. 3,843,732; 3,824,195; 3,789,078; 3,709,951. The catalyst preferred for use in the present invention is prepared by forming a Sn/P/O composition with a catalyst structure containing from about 0.1 to about 14 weight percent phosphorous. This structure is then impregnated with an additional amount of phosphorous ranging from about 1 to about 3.5 weight percent such that the total phosphorous content of this Sn/P/O composition, called here the first composition, does not exceed about 15 weight percent. The tin content of the first composition will depend upon the amount of phosphorous present but will generally be in the range of from about 15 to about 75 weight percent. The remainder of the composition contains oxygen in amounts sufficient to satisfy the valence requirements of the phosphorous and tin. This first composition is dried, calcined, and impregnated with lithium in an amount from about 0.1 to about 10 weight percent based on the Sn/P/O composition. The resulting second composition is subsequently dried and calcined.

The specific catalyst used in an example herein was 72 weight percent $SnO_2$, 3 weight percent $Li_2O$, and 25 weight percent $P_2O_5$. This is equivalent on a free metal basis to 50 weight percent Sn, 2 weight percent Li and 10 weight percent P.

Generally air is used as the oxidant in this invention although pure oxygen or any gaseous mixture containing oxygen can also be used. When air is used, the mole ratio of air to olefin is generally between about 20:1 to about 1:1. The reaction temperature is generally in the range of about 300° C. to 500° C. The reaction pressure can be from 0 to 500 psig. The process is not dependent upon any particular method of recovery of the useful products of oxidation. The product may be recovered by chilling the reaction products and fractionating the desired unsaturated aldehyde by distillation.

The following example serves to illustrate this invention.

Into a 14 inch×0.5 inch vertical 316 stainless steel tube lined with a 0.5 inch removable glass liner and fitted with a 3 mm glass thermowell and sealed at the bottom except for several approximately 1 mm holes which allow gas passage was charged 5.46 grams (5 milliliters) of a 72 weight percent $SnO_2$, 3 weight percent $Li_2O$, and 25 weight percent $P_2O_5$ catalyst. The glass liner was press-sealed to the reactor at the top with thin 97 weight percent pure asbestos paper wrapping. The thermowell was sealed into the 316 stainless steel head using Teflon ® polymer ferrules. The associated feed system consisted of gas cylinders feeding through rotameters into a manifold which was attached through a 2 inch×0.25 inch fitting packed with quartz chips for gas mixing to the head of the reactor. Two ports for sampling gases by GLC analysis were provided, one in the line just ahead of the reactor head and one at the reactor outlet. The head contained a pressure gauge and valves distributed to regulate gas flows. The entire apparatus was heated with electrical heating tape. While the reactor was being slowly heated to reaction temperature (above 200° C.), air (191 milliliters per minute, STP) and propylene (9.3 milliliters per minute, STP) was passed downwardly through the catalyst bed at a 2400 GHSV (Gas Hourly Space Velocity) and a contact time of 1.5 second. The reactor was operated at a temperature of about 400° C. for several minutes, a sample was analyzed by GLC, and the temperature then increased to a temperature level of 450° C. and another sample again analyzed. After analysis at the 450° C. level, the reactor was cooled to 350° C. and the process repeated at 25° C. increments until a reaction temperature of 425° C. was reached. In this way, the optimum reaction temperature at the particular gas flow was determined. The effluent was analyzed by GLC using a 6 foot×¼ inch column packed with Mole Sieve 13x/Porapak ® (from Alltech Associates) with a helium gas flow of 60 milliliters per minute and a column temperature of 25°–110° C. The resulting data which are listed in Table I indicate the highest propylene conversion occurs at about 425° C. with the highest acrolein selectivity at about 350°–375° C. The data also suggest that selectivity can be further improved by re-using catalyst although propylene conversion is decreased. This was shown by cooling the reactor temperature from 425° C. to 350° C. and repeating the 25 degree interval increases in reaction temperature.

TABLE I.

Air Oxidation of Propylene

Feed: 191 mL Air/min
  9.3 mL Propylene/min
  200 psig
Catalyst: 72 weight percent SnO$_2$/3 weight percent Li$_2$O/ 25 weight percent P$_2$O$_5$

| Reaction Temp. °C. | % Propylene Conversion | Acrolein$^a$ by GLC m mol/min | % Selectivity |
|---|---|---|---|
| 200 | 5 | 0 | 0 |
| 250 | 11 | 0 | 0 |
| 300 | 16 | trace | trace |
| 350 | 18 | 0.018 | 23 |
| 400 | 30 | 0.027 | 21 |
| 450 | 98 | 0.072 | 17 |

(Reactor cooled to 350° C. and reaction continued with same catalyst)

TABLE I.-continued

Air Oxidation of Propylene

Feed: 191 mL Air/min
  9.3 mL Propylene/min
  200 psig
Catalyst: 72 weight percent SnO$_2$/3 weight percent Li$_2$O/ 25 weight percent P$_2$O$_5$

| Reaction Temp. °C. | % Propylene Conversion | Acrolein$^a$ by GLC m mol/min | % Selectivity |
|---|---|---|---|
| 350 | 11 | 0.029 | 58 |
| 375 | 9 | 0.024 | 60 |
| 400 | 23 | 0.022 | 22 |
| 425 | 95 | 0.024 | 6 |

$^a$No propylene oxide was found

We claim:

1. A method for preparing aldehyde from aliphatic olefin represented by the formula

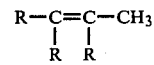

wherein each R can be hydrogen or any alkyl group having one to 8 carbon atoms, and each R can be the same or different from the other R's, comprising contacting said aliphatic olefin with an oxygen containing gas at an elevated temperature in the presence of a composition comprising phosphorus, tin, oxygen and lithium.

2. A method of claim 1 wherein said composition comprises a first composition comprising from about 15 to about 75 weight percent tin, from about 0.1 to about 15 weight percent phosphorous, and the remainder oxygen which is dried, calcined, and impregnated with lithium to form a second composition containing said lithium in an amount of about 0.1 to about 10 weight percent based on said first composition.

3. A method of claim 1 or 2 wherein the oxygen containing gas is air present in mole ratio of air to aliphatic olefin in the range of about 20:1 to about 1:1.

4. A method of claim 1 or 2 wherein said aldehyde is acrolein and said aliphatic olefin is propylene.

5. A method of claim 3 wherein said second composition contains about 50 weight percent tin, about 2 weight percent lithium and about 10 weight percent phosphorous.

6. A method of claim 5 wherein said aldehyde is acrolein and said aliphatic olefin is propylene.

* * * * *